United States Patent
Reindl et al.

(10) Patent No.: US 6,852,434 B2
(45) Date of Patent: Feb. 8, 2005

(54) FUEL CELL ASSEMBLY WITH AN IMPROVED GAS SENSOR

(75) Inventors: Michael Reindl, Markdorf (DE); Thomas Roesch, Dornstadt (DE); Ralf Erich Moos, Friedrichschafen (DE); Thomas Alfred Birkhofer, Immenstad (DE); Wilhelm Mueller, Salem-Buggensegel (DE); Ralf Wolfgang Mueller, Aulendorf (DE)

(73) Assignee: Ballard Power Systems Inc., Burnaby (CA)

( * ) Notice: Subject to any disclaimer, the term of this patent is extended or adjusted under 35 U.S.C. 154(b) by 388 days.

(21) Appl. No.: 09/738,074

(22) Filed: Dec. 15, 2000

(65) Prior Publication Data

US 2002/0110713 A1 Aug. 15, 2002

Related U.S. Application Data

(60) Provisional application No. 60/172,053, filed on Dec. 23, 1999.

(51) Int. Cl.[7] ............................................... H01M 8/18
(52) U.S. Cl. .............................. 429/22; 429/23; 429/30; 204/400; 29/729
(58) Field of Search ............................... 429/22, 13, 23, 429/30, 400, 401, 415, 432, 729, 738, 745; 204/400, 401, 415, 432, 783; 29/729, 738, 745

(56) References Cited

U.S. PATENT DOCUMENTS

| | | | | |
|---|---|---|---|---|
| 4,578,174 A | * | 3/1986 | Kato et al. | 204/429 |
| 4,595,485 A | * | 6/1986 | Takahashi et al. | 204/406 |
| 4,943,330 A | * | 7/1990 | Iino et al. | 156/89.16 |
| 5,498,487 A | * | 3/1996 | Ruka et al. | 429/20 |
| 5,518,601 A | * | 5/1996 | Foos et al. | 204/415 |
| 6,129,825 A | * | 10/2000 | Mallory et al. | 204/415 |
| 6,461,751 B1 | * | 10/2002 | Boehm et al. | 429/13 |

FOREIGN PATENT DOCUMENTS

| | | |
|---|---|---|
| JP | 60-208059 | 10/1985 |
| JP | 60-212966 | 10/1985 |
| JP | 61-279071 | 12/1986 |
| JP | 64-089155 | 4/1989 |
| JP | 01-239772 | 9/1989 |

* cited by examiner

Primary Examiner—Michael Barr
Assistant Examiner—Monique Wills
(74) Attorney, Agent, or Firm—Seed IP Law Group PLLC

(57) ABSTRACT

A fuel cell assembly has an improved gas sensor. The improved sensor measures the gas concentrations in the interior fluid passages within a fuel cell assembly or within fluid passages employed to transport reactant fluid streams to or from the fuel cell(s). The improved sensor is particularly suited for use in the environment within the reactant fluid passages of a solid polymer fuel cell assembly and is tolerant to the presence of water. The sensor employs an active electrode; a passive electrode; and an electrolyte in contact with both electrodes. The electrolyte is disposed on a substrate and a heater is located in thermal contact with the substrate for heating the substrate and the electrolyte.

27 Claims, 8 Drawing Sheets

FUEL CELL ASSEMBLY WITH AN IMPROVED GAS SENSOR

This application claims benefit of 60/172,053 filed Dec. 23, 1999.

FIELD OF THE INVENTION

The present invention relates to a fuel cell combined with an improved gas sensor. In particular, the improved gas sensor may be employed to measure a gas concentration in a reactant fluid passage within a fuel cell.

BACKGROUND OF THE INVENTION

Electrochemical fuel cells convert reactants, namely, fuel and oxidant fluid streams, to generate electric power and reaction products. Electrochemical fuel cells generally employ an electrolyte disposed between two electrodes, namely a cathode and an anode. The electrodes each comprise an electrocatalyst disposed at the interface between the electrolyte and the electrodes to induce the desired electrochemical reactions.

The fuel fluid stream supplied to a fuel cell anode typically comprises hydrogen, which may be, for example, substantially pure gaseous hydrogen, or a dilute hydrogen stream such as a reformate stream. Other fuels such as methanol or dimethyl ether may be used instead of hydrogen. The oxidant fluid stream supplied to a fuel cell cathode typically comprises oxygen, which may be, for example, substantially pure gaseous oxygen, or a dilute oxygen stream such as air.

In solid polymer fuel cells, the water content in the reactant fluid streams supplied to and exhausted from the fuel cell may, in some cases, cause problems for conventional gas sensors. A solid polymer fuel cell employs an electrolyte that is an ion (typically proton) conductive solid polymer membrane. This membrane also separates the hydrogen supplied to the anode from the oxygen supplied to the cathode. For the solid polymer membrane to be an effective proton conductor, it must be kept sufficiently hydrated. If the membrane becomes dehydrated, in addition to reduced proton conductivity, structural failures may occur at the dehydrated portions of the membrane. For example, structural failures may result in cracks and/or holes and associated reactant leaks. Accordingly, one or both of the fuel and oxidant streams are typically humidified to ensure that these streams carry a sufficient quantity of water to prevent membrane dehydration. In addition to humidification water, the oxidant exhaust stream also typically comprises product water, which is produced by the desired electrochemical reactions that are induced at the fuel cell cathode. Accordingly, there can be a significant amount of water in the fuel cell reactant streams. For example, it is not uncommon for the water content in an oxidant exhaust stream to be about one-third by volume. The presence of such significant amounts of water in the reactant streams can hinder the operation of some conventional commercially available gas sensors, reducing the reliability and accuracy of such sensors.

Relatively low operating temperatures are another characteristic of the environment within the reactant fluid passages of solid polymer fuel cells. Generally, the temperature is less than 100° C. within the reactant fluid passages of a solid polymer fuel cell. This temperature presents a problem for conventional gas sensors which employ a solid oxide electrolyte because solid oxides are better ion conductors, and thus generally more effective, at much higher temperatures. Due to the changes in the vapor content of fluid streams in fuel cells, thermal conductivity sensors often used for ambient hydrogen detection are not generally suitable for use in fuel cell applications.

In a fuel cell, gas sensors, such as hydrogen or oxygen gas sensors may be used to monitor the respective gas concentration in the fuel and/or oxidant streams. The concentration of the reactant gases, at particular locations within the reactant streams, may be measured and used as an indicator of the fuel cell performance and operating efficiency. For example, if there is an excessive amount of gaseous hydrogen in the fuel stream exhausted from the fuel cell, this indicates poor operating efficiency, or if there is an increase in hydrogen concentration in the oxidant exhaust stream, this may be an indication of a leak in the membrane or a shortage of oxidant supplied to the cathode.

The present fuel cell assembly incorporates an improved reactant gas sensor that operates reliably and accurately when located in a fuel or oxidant fluid stream passage within a solid polymer fuel cell.

SUMMARY OF THE INVENTION

A fuel cell assembly with an improved gas sensor comprises:
  (a) at least one fuel cell, comprising:
    an anode;
    a cathode;
    an electrolyte (preferably a solid polymer electrolyte) interposed between the anode and the cathode;
    a fuel passage in fluid communication with the anode for directing a fuel stream to and from the anode;
    an oxidant passage in fluid communication with the cathode for directing an oxidant stream to and from the cathode; and
  (b) an electrochemical sensor associated with one of the fuel and oxidant passages for measuring the concentration of a gas in a respective one of the fuel and oxidant streams, the sensor comprising:
    an active electrode;
    a passive electrode;
    an electrolyte in contact with the active electrode and the passive electrode;
    a substrate upon which the electrolyte is disposed; and
    a heater in thermal contact with the substrate for heating the substrate and thereby heating the electrolyte.

In preferred embodiments, the sensor's electrolyte film has a thickness less than 100 microns, and preferably in the range of about 5 to 25 microns. In some embodiments the thickness may be about 1 micron. The electrolyte preferably comprises a solid oxide electrolyte, comprising a material such as, for example, one selected from the group consisting of $ZrO_2$, $CeO_2$ and $HfO_2$. Preferred are yttrium or calcium doped $ZrO_2$. In one embodiment, both of the substrate and the electrolyte are made from the same material, and the substrate is unitary with the electrolyte. The substrate is preferably a good thermal conductor and an electrical insulator.

In a preferred embodiment, the passive electrode further comprises a coating that fluidly isolates the passive electrode from the surrounding atmosphere. For example, the coating may comprise glass or ceramic. Isolating the passive electrode ensures that it remains passive (that is, the coating prevents any reactions from occurring at the passive electrode that might influence the accuracy of the sensor).

In a preferred arrangement the active and passive electrodes are spaced apart by an average distance of between 0.1 millimeter and 10 millimeters. Preferably, the passive electrode and the active electrode may each have a thickness between 0.0001 millimeter and 1 millimeter. The active electrode preferably comprises platinum and the passive electrode preferably comprises gold.

In a preferred embodiment, the heater comprises a heating element that heats the electrolyte to a temperature between 300° C. and 650° C.; that is, the heater provides heat for raising the temperature of the electrolyte so that the electrolyte has an ion-conductance value greater than $10^{-4}$ $(\Omega cm)^{-1}$. The heating element, for example, may comprise a resistor coil electrical circuit. There are many methods and corresponding apparatuses that may be used to control the temperature of the heater. For example, to regulate temperature, the heater may further comprise a device for measuring heater voltage and current so that electrical resistance of the resistor coil may be calculated by dividing the heater voltage by the heater current. Alternatively, the heater may further comprise a separate electrical circuit for measuring the temperature of the electrochemical sensor. The separate electrical circuit may further comprise its own resistor, distinct from the resistor coil portion of the heater. A temperature controller may be employed for changing the current or supply voltage of the heater to adjust the temperature of the sensor to improve the ion conductivity of the electrolyte. In a further preferred embodiment, a separate electrical circuit for measuring the temperature may be located on one side on the substrate of the sensor. In another embodiment one of the electrodes has a shape, for example a coil shape, that make it suitable for measuring the temperature of the electrode itself. In this case the electrode itself serves as a temperature dependent resistor for temperature sensing.

The heater may further comprise a coating, such as, for example, a coating comprising glass or ceramic, which fluidly isolates the heater from the surrounding atmosphere.

In a preferred embodiment, the heater is provided with heating energy from at least one fuel cell of the fuel cell assembly.

The electrochemical sensor detects and measures the concentration of a target gas with a sensitivity within a range from 1 ppm to 20,000 ppm. The sensor emits a signal representative of the target gas concentration within the sensitivity range. For example, the target gas concentration may be measured by employing an electrical circuit for measuring the voltage difference between the active electrode and the passive electrode, where the voltage difference correlates to target gas concentration.

In a preferred embodiment of the fuel cell assembly, the target gas is hydrogen and the sensor measures the concentration of hydrogen in the oxidant stream. In this preferred embodiment, the sensor is preferably located in the oxidant passage downstream of the cathode. In a preferred arrangement, the sensor is located within an interior oxidant or fuel stream passage within the fuel cell assembly, such as, for example, an interior fluid passage within an end plate of the fuel cell assembly. It is generally preferable to locate the sensor within the fuel cell assembly because when the sensor is located further downstream it is less accurate because the target gas may be reactive with the other components of the fluid stream.

In one embodiment, the fuel cell assembly comprises at least two electrochemical sensors, with a first electrochemical sensor for detecting a hydrogen gas concentration in the oxidant stream and a second electrochemical sensor for detecting an oxygen gas concentration in the fuel stream.

The preferred method of fabricating an electrochemical gas sensor for a fuel cell assembly comprises:

(a) placing an electrolyte on a substrate equipped with a heating element, and heating said substrate and said electrolyte to a temperature above about 600° C., and preferably above 1100° C.;

(b) placing an active electrode (preferably comprising platinum) on the electrolyte;

(c) heating the substrate, the electrolyte, and the active electrode to a temperature above about 600° C., and preferably above 900° C.;

(d) placing a passive electrode (preferably comprising gold) on the electrolyte; and (e) heating the substrate, the electrolyte, the active electrode, and the passive electrode to a temperature above 400° C., and preferably above 800° C., but below the melting temperature of the passive electrode;.

In a preferred method the electrolyte has a thickness less than 100 microns and the electrolyte comprises a material selected from the group consisting of $ZrO_2$, $CeO_2$ and $HfO_2$. Preferred are yttrium- or calcium-doped $ZrO_2$. Electrical wires or an electrical connector are attached to the terminal ends.

A preferred method further comprises depositing a fluid impermeable coating, such as, for example, glass, ceramic or glass ceramic, over the heating element.

DETAILED DESCRIPTION OF PREFERRED EMBODIMENT(S)

Figure 1:
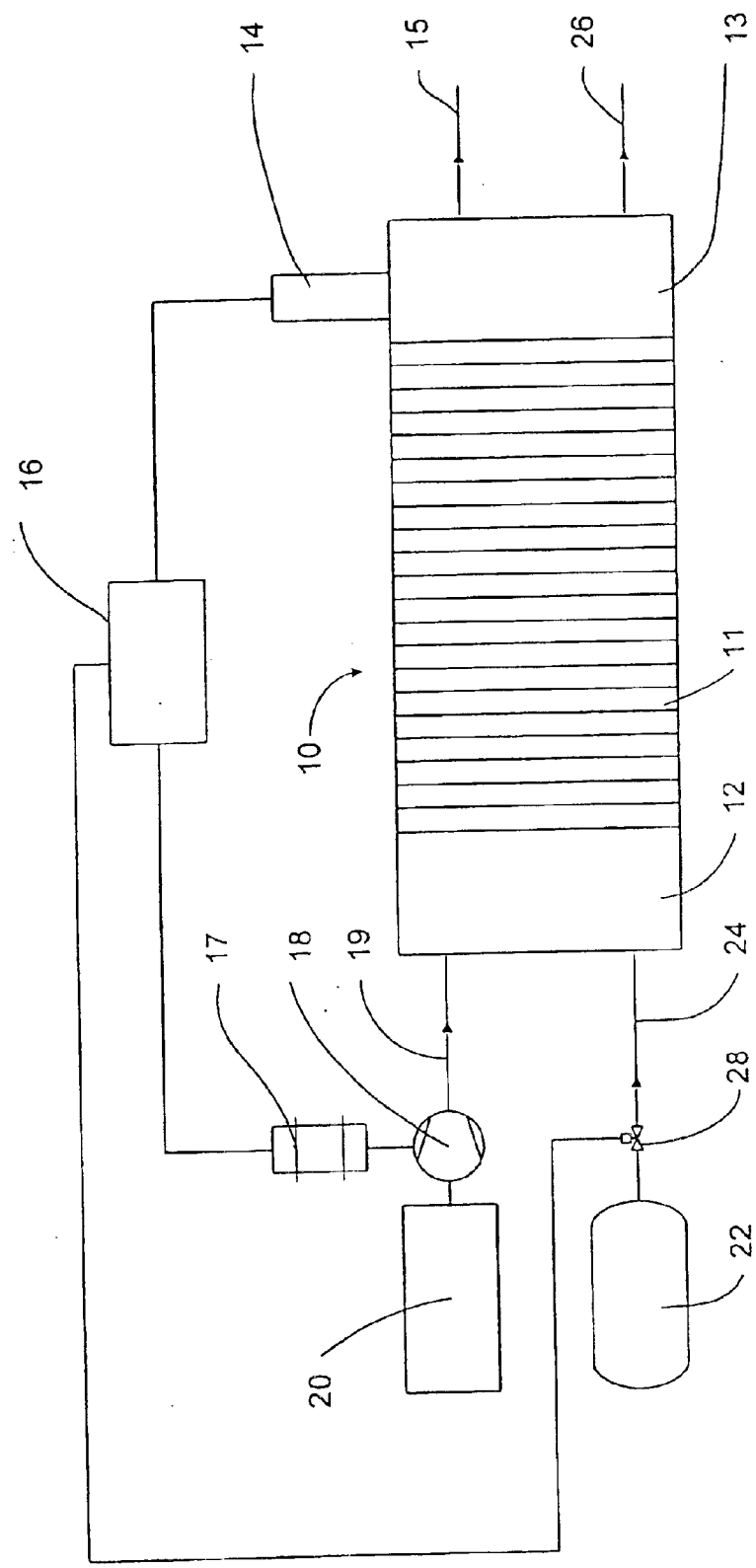
FIG. 1 is a schematic diagram showing a fuel cell assembly with a gas sensor probe located on an end plate for sensing a reactant gas concentration within a reactant stream passage within the end plate.

FIG. 1 is a schematic diagram of a fuel cell stack 10 comprising at least one fuel cell 11 between end plate assemblies 12 and 13. In the embodiment illustrated by FIG. 1, fuel cell stack 10 comprises a plurality of fuel cells 11. Fuel cell stack 10 further comprises a gas sensor 14 associated with a fuel cell reactant stream passage (not shown in FIG. 1) within end plate assembly 13. Controller 16 receives data indicative of various fuel cell operating parameters, including, for example, an output signal from sensor 14.

The functions of controller 16 include controlling the amount of reactants supplied to fuel cell stack 10. For example, FIG. 1 shows controller 16 linked to motor 17 for regulating the speed of compressor 18 which delivers an oxidant fluid stream from oxidant supply system 20 to fuel cell stack 10 through oxidant supply passage 19. When the oxidant is air, oxidant supply system 20 typically further comprises filters and/or other air purification devices. When the oxidant is compressed oxygen, oxidant supply system 20 may be more similar to depicted fuel supply system 22 and a valve may be used to regulate oxidant supply instead of compressor 18. The fuel exhaust stream exits fuel cell stack 10 via fuel exhaust passage 26. Controller 16, is also shown linked to valve 28 for regulating the supply of fuel from fuel supply system 22 to fuel cell stack via fuel supply passage 24. Fuel supply system 22 may comprise a fuel storage device such as, for example, a pressure vessel for holding compressed gas, a non-pressurized fuel tank for holding a liquid fuel, or a solid storage media such as a metal hydride saturated with fuel. Fuel supply system 22 may further comprise a reformer system for converting hydrogen-rich fuels, such as hydrocarbons, into substantially pure hydrogen.

In a preferred arrangement, sensor 14 is associated with fuel cell stack 10 by exposing the sensing portion of sensor 14 to a reactant fluid passage within end plate assembly 13. In a preferred embodiment, the target gas is hydrogen and sensor 14 acts as a hydrogen sensor and is associated with an internal oxidant exhaust passage or manifold within end plate assembly 13. Alternatively, sensor 14 may be located downstream of fuel cell stack 10. For example, sensor 14 may be associated with external oxidant exhaust passage 15. However, it is preferable to locate sensor 14 closer to fuel cells 11 so that there is less opportunity for any hydrogen gas to react with excess oxygen before encountering sensor 14. Similarly, for an oxygen sensor located in the fuel exhaust stream, it is preferable to locate the oxygen sensor as close as possible to fuel cells 11.

Figure 2:
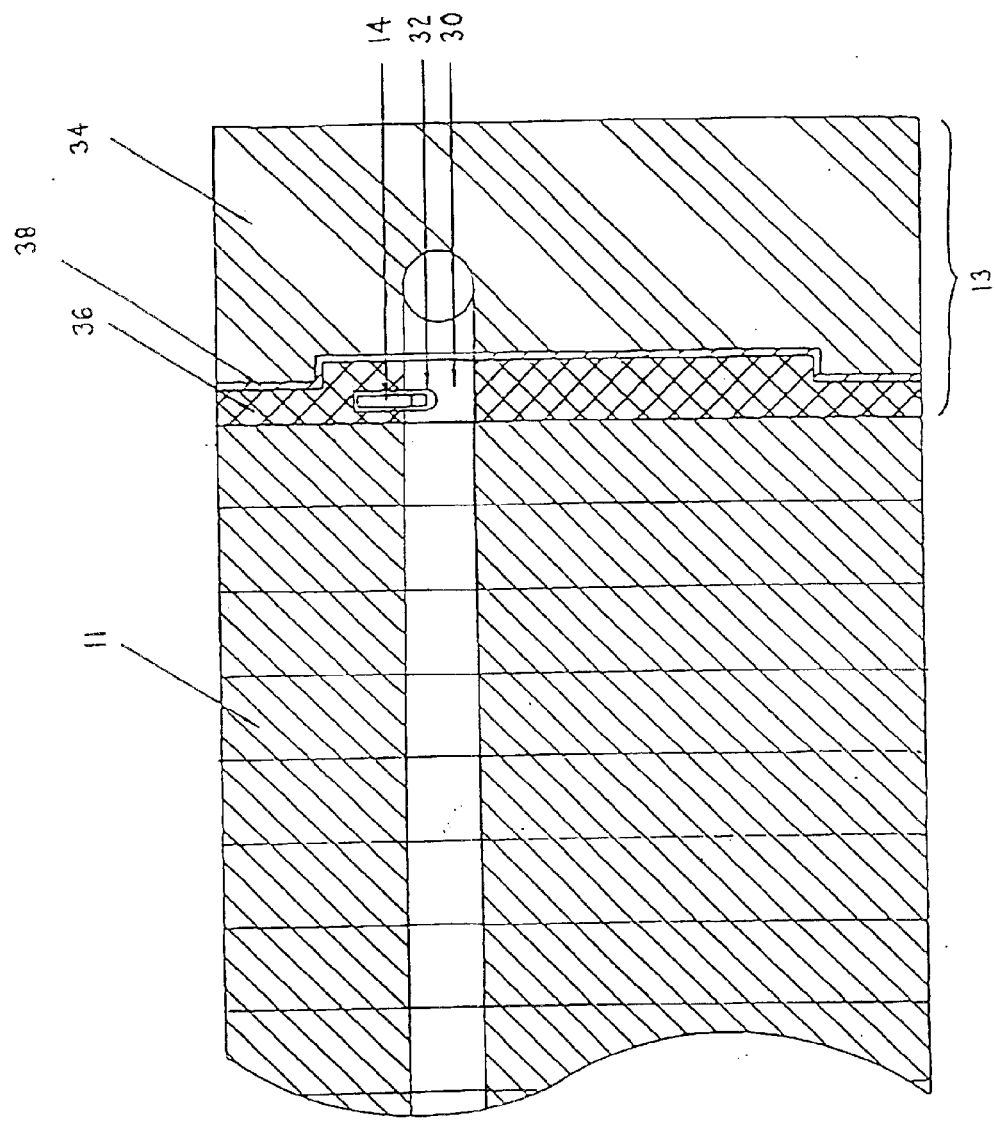
FIG. 2 is a partial cross-sectional view through a fuel cell assembly depicting the location of a gas sensor in a fluid passage located within the interior of the end plate.

FIG. 2 is a partial cross-sectional view of a fuel cell stack depicting an embodiment wherein sensor 14 is located in internal fluid passage 30 within end plate assembly 13. As described above, for applications where sensor 14 is measuring the concentration of a gas in a reactant exhaust stream, it is preferable to locate sensor 14 as close as possible to fuel cells 11. Sensor 14 comprises a sensing portion that protrudes into fluid passage 30 that is internal to end plate assembly 13. Sensor 14 may be provided with a protective screen 32 that is gas permeable and not catalytically active. Screen 32 may be, for example, a porous layer or film such as a perforated material or a woven mesh. Further, screen 32 may be fabricated from materials such as, for example, stainless steel, sintered metal, sintered ceramic, or plastic. The preferred screen materials are compatible with the operating conditions within the fluid passages of fuel cells 11. For example, the screen material is preferably non-corrosive when exposed to de-ionized water, methanol, glycol or oxygen radicals. The reactant exhaust stream typically comprises liquid water and water vapor. The primary purpose of screen 32 is to provide mechanical protection for sensor 14 but another benefit is that it helps to keep liquid water away from sensor 14. Screen 32 is preferably hydrophobic so that water does not collect on the screen and reduce the gas permeability of screen 32. Because the operating temperature of sensor 14 is preferably between 300° C. and 650° C., water generated at the surface of the active sensor electrode is generally in the vapor phase and can pass through screen 32 as vapor.

End plate assembly 13 comprises end plate 34 and compression plate 36. End plate 34 is held in a substantially fixed position relative to an opposing end plate at the opposite end of the fuel cell stack (not shown). End plate assembly 13 provides a means (not shown) such as springs or a hydraulic or pneumatic piston for urging compression plate 36 away from end plate 34 and towards the opposing end plate to compress fuel cells 11. Resilient seal 38 prevents reactant and cooling fluids from leaking from end plate assembly 13. In an alternative arrangement, the fluid passages within end plate assembly are located entirely within compression plate 36 so that seals are not required between compression plate 36 and end plate 34.

Figure 3A:
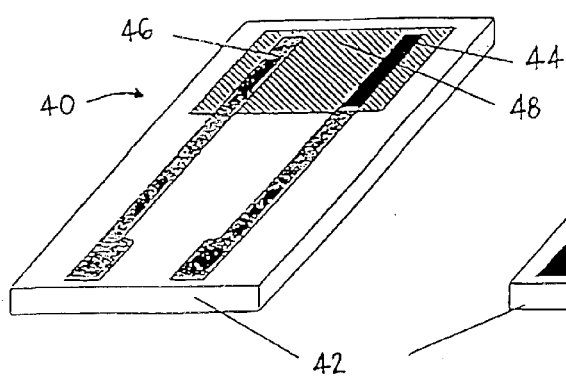
FIGS. 3a and 3b are perspective views of opposing surfaces of an embodiment of an improved gas sensor.
Figure 3B:
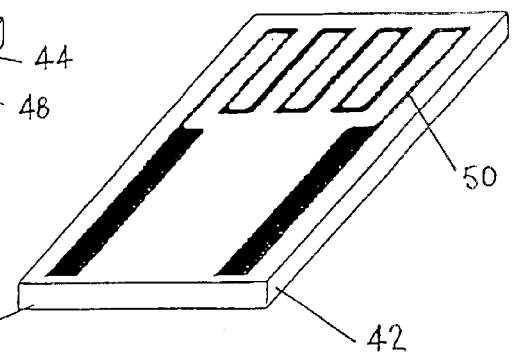

FIGS. 3a and 3b are perspective views of opposing surfaces of an embodiment of an improved gas sensor 40. As shown in FIG. 3a, depicted sensor 40 comprises substrate 42 upon which a layer of solid or pasteous electrolyte 48 is disposed. Substrate 42 is a material that is thermally conductive and an electrical insulator, such as, for example, $Al_2O_3$. Active electrode 44 and passive electrode 46 overlay substrate 42 and contact electrolyte 48.

In applications where sensor 40 is employed to measure the concentration of hydrogen in an atmosphere comprising hydrogen and oxygen, active electrode 44 typically comprises platinum that catalytically induces hydrogen and oxygen to react with each other to produce water. Preferably no electrochemical reactions occur at passive electrode 46. Passive electrode 46 provides a reference point for comparison to active electrode 44. It is important for passive electrode 46 to be a reliable reference point because it is the different electrochemical activity at the active and passive electrodes that results in different electrode potentials; the potential difference between the active and passive electrodes is dependent on the concentration of the target gas in the reactant stream.

Passive electrode 46 may be made from any electrically conductive metal. However, in preferred embodiments, passive electrode 46 comprises an inert material (or at least a metal with lower catalytic activity) such as, for example, pure gold. While gold is a generally inert metal, impurities in the gold may induce reactions to occur at passive electrode 46. Accordingly, the material composition of passive electrode 46 is preferably pure gold, or at least substantially pure gold, so that electrochemical reactions are not catalytically induced thereon. "Substantially pure gold" is defined herein as meaning a degree of purity that allows the material to be employed as a passive electrode to provide a reliable reference point (that is, if any reactions do occur at the passive electrode, they are to such a small degree that they do not significantly influence the accuracy and reliability of sensor 40 within the sensor's desired concentration operational range).

FIG. 3b shows the surface of substrate 42 that is opposite to the surface shown in FIG. 3a. A heating device such as an electrical circuit is employed to heat the substrate to regulate the temperature of electrolyte 48. Accordingly, the electrical circuit comprises heating element 50 located directly underneath electrolyte 48. The heating device may be regulated by adjusting the electrical resistance in the heating circuit to determine the temperature, since electrical resistance is a function of temperature. Temperature may be adjusted by controlling the amount of current directed to heating element 50.

Figure 4:
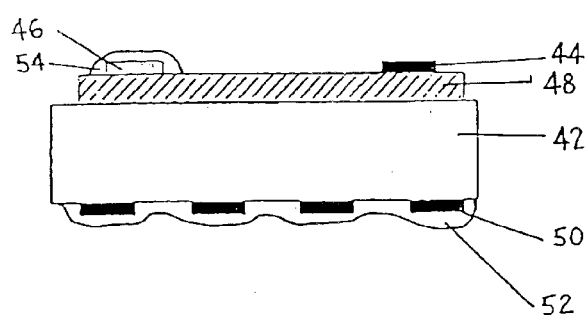
FIG. 4 is a cross-sectional view of the sensor of FIGS. 3a and 3b.

FIG. 4 is a cross-section view of a sensor like sensor 40 of FIGS. 3a and 3b. Like reference numbers are used to denote like components. Substrate 42 supports electrolyte layer 48 and overlaying active and passive electrodes 44 and 46 respectively. Substrate 42 also supports the electrical circuit comprising heating element 50 for heating electrolyte 48. FIG. 4 also depicts additional features, not shown in FIGS. 3a and 3b, that may be employed in embodiments of the improved sensor. For example, heating element 50 may be fluidly isolated from the surrounding atmosphere by fluid impermeable coating 52. In a preferred embodiment, coating 52 is glass, ceramic or a glass ceramic. Passive electrode 46 may also be fluidly isolated from the surrounding environment by fluid impermeable coating 54, which may also be glass, ceramic or a glass ceramic. The firing temperature of the coating is preferably less than that of the passive electrode material. Glass is a preferred coating because of its low electrical conductivity. A glass ceramic coating with an adapted thermal expansion coefficient is particularly preferred. Another preferred coating is a sintered ceramic, such as, for example, $Al_2O_3$. A further method for applying the coating would involve bonding a sheet of appropriate coating material on to the electrode structure, for example, using a ceramic glue.

Figure 5:
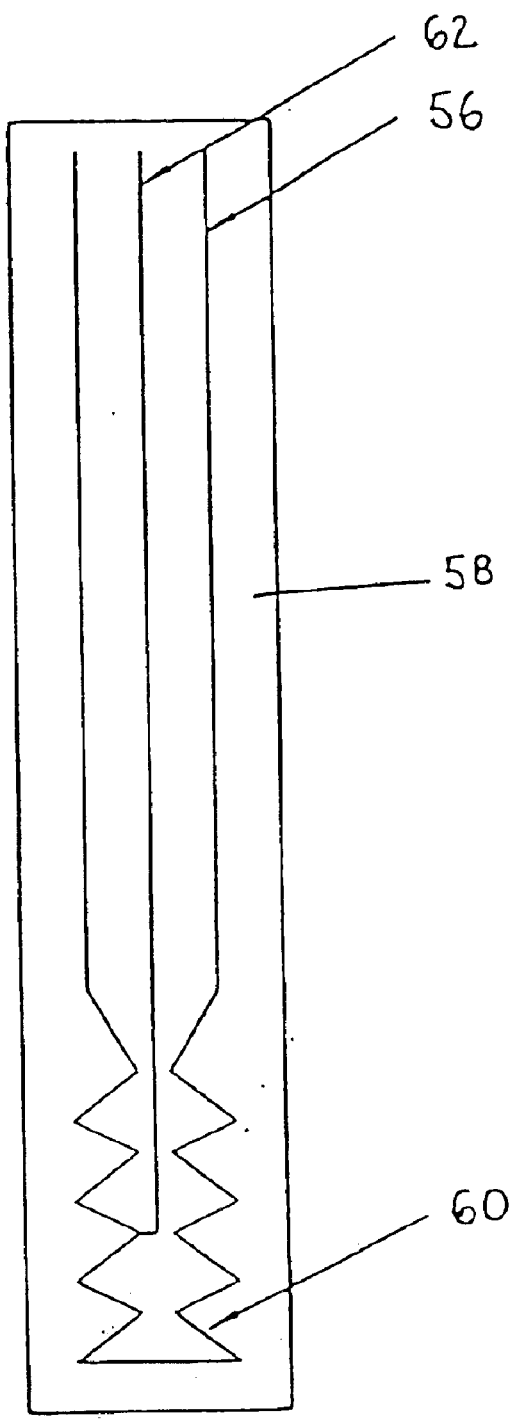
FIG. 5 is a plan view of a gas sensor showing an embodiment of the heater.

FIG. 5 is a plan view of a gas sensor depicting electrical heating device 56 disposed on a major surface of substrate 58. Like other embodiments, electrical heating device 56 comprises heating element 60 positioned opposite to an electrolyte on the opposing major surface (not visible in FIG. 5). In this embodiment, however, electrical heating device 56 comprises three electrical leads. Middle electrical lead 62 provides a means for monitoring the electrical resistance for determining the sensor temperature. The ion conductivity of the solid oxide electrolyte is dependent upon its temperature so it is important to monitor and accurately control the temperature of the sensor using a temperature control means such as heating device 56.

In an alternative embodiment, the sensor may employ a separate electrical circuit for monitoring the sensor temperature. In this alternative embodiment, the sensor would comprise at least six electrical leads, specifically, one lead for the active electrode, one lead for the passive electrode, two leads for the electrical heating device, and two leads for the temperature monitoring circuit. The electrical circuit for monitoring the sensor temperature can be located on either major surface of the sensor substrate, so long as it is in close proximity to the solid oxide electrolyte.

Figure 6A:
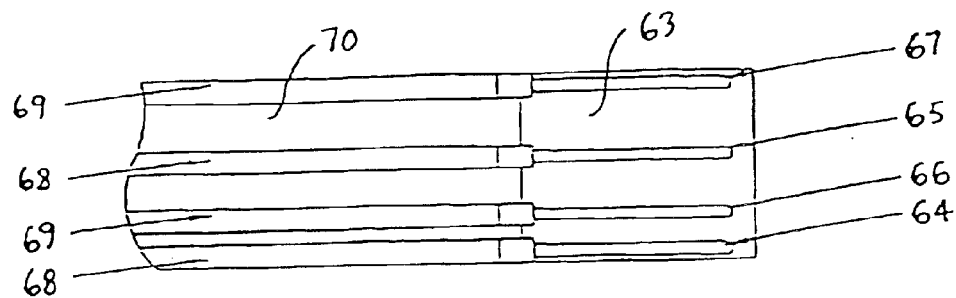
FIGS. 6a, 6b and 6c are plan views of gas sensors depicting alternate arrangements for the active and passive electrodes.
Figure 6B:
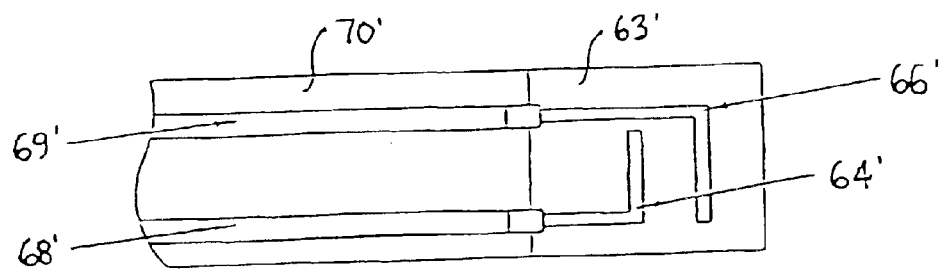
Figure 6C:
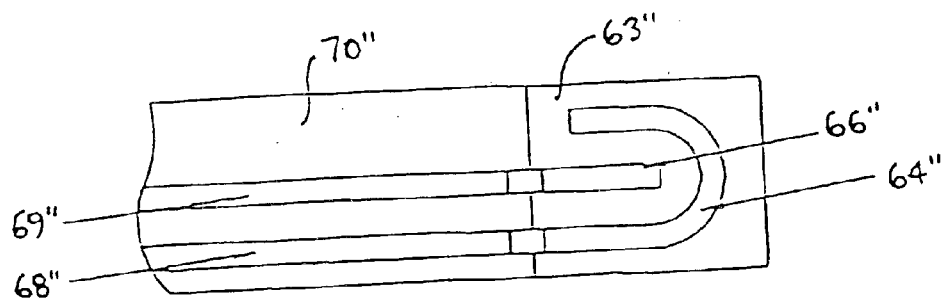

FIGS. 6a through 6c are partial plan views of different sensors showing alternative arrangements for the active and passive electrodes. These alternate embodiments show that arrangements may be employed other than the arrangement shown in FIG. 3a. In FIG. 6a, there are four sensor electrodes. Active electrodes 64 and 65 alternate with passive electrodes 66 and 67 and all of these electrodes are in contact with solid electrolyte 63. Active electrode 64 and passive electrode 66 are spaced closer to one another than active electrode 65 and passive electrode 67. The distance between the electrodes influences the signal and its sensitivity. Accordingly, with the embodiment of FIG. 6a, the sensitivity of the sensor can be changed by switching between electrodes 64 and 66, and electrodes 65 and 67. In the illustrated embodiments, active electrode electrical leads 68 and passive electrode leads 69 may be made from a different material than the electrodes. Electrical leads 68 and 69 are supported by substrate 70. Preferably electrical leads 68 and 69 are made from materials that are less expensive than the electrode materials and that have good electrical conductivity. In the embodiment of FIG. 6b, active electrode 64' and passive electrode 66' each have a right-angled corner. Substrate 70' supports solid electrolyte layer 63' and electrical leads 68' and 69'. In the embodiment of FIG. 6c, active electrode 64" curves around the end of passive electrode 66". Like the other embodiments, substrate 70" supports solid electrolyte layer 63" and electrical leads 68" and 69". In the embodiments of FIGS. 6b and 6c, one electrode is longer than the other electrode. By having one electrode much shorter than the other, the quantity of electrode material can be reduced and reaction times may be shortened. The embodiment of FIG. 6c may give better signal stability.

Figure 7:
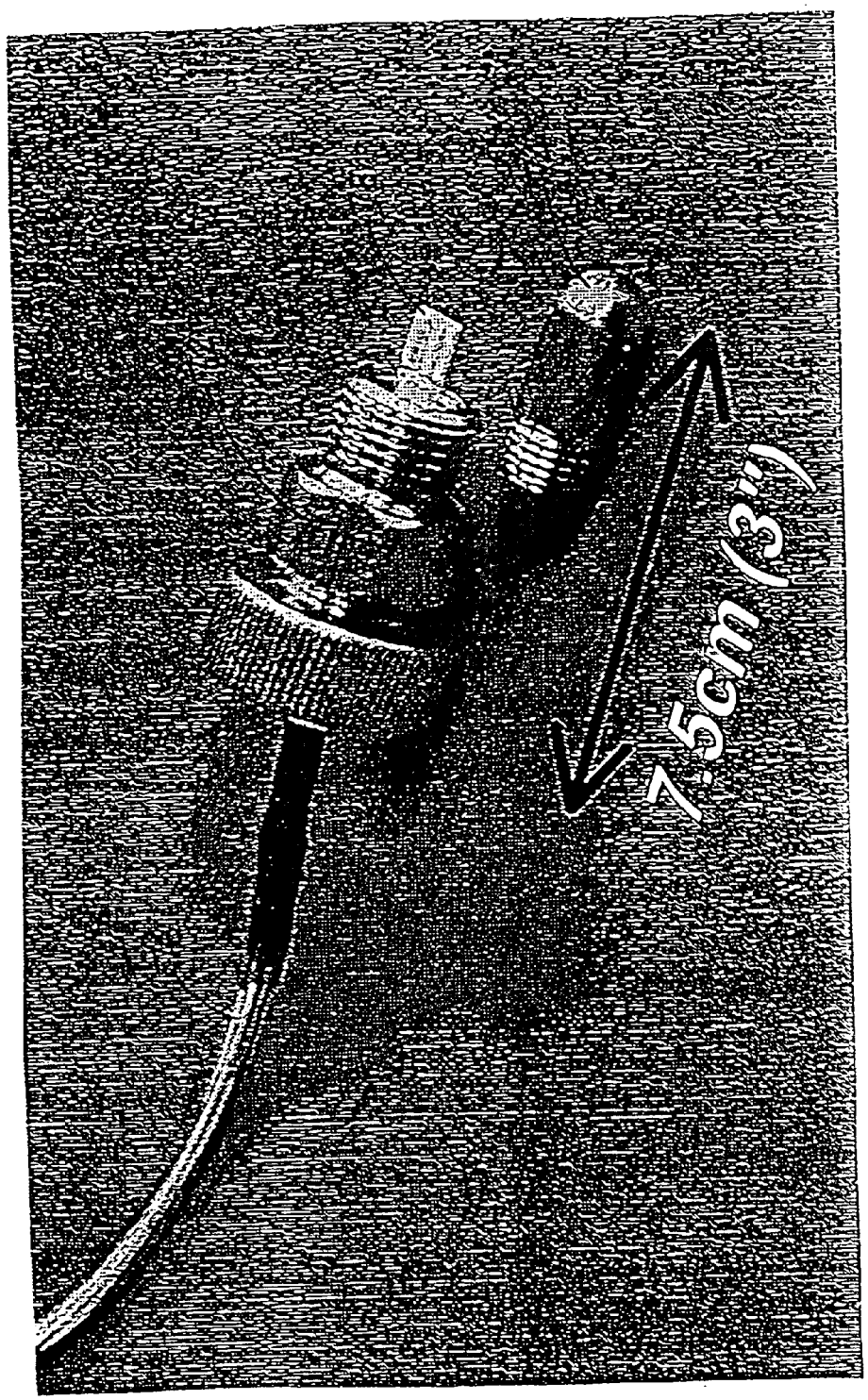
FIG. 7 is a perspective view of a sensor mounted in a housing with the protective screen removed.

FIG. 7 is a perspective view of an embodiment of a gas sensor mounted in housing 72 with protective screen 74 removed. Wires 76 are connected to the electrical leads (not shown) of sensor 78. Protective screen 74 has a threaded base for mounting onto housing 72. Housing 72 has its own threaded portion for mounting the housing to a fuel cell assembly. Those skilled in the art will appreciate that the shape and configuration of the housing is not critical to the operation of the sensor provided housing 72 positions sensor 78 in the fluid passage of the reactant fluid stream that is being monitored. The length of the housing depicted in FIG. 7 is about 7.5 cm (about 3 inches) from the tip of screen 74 to the base of housing 72.

Figure 8:
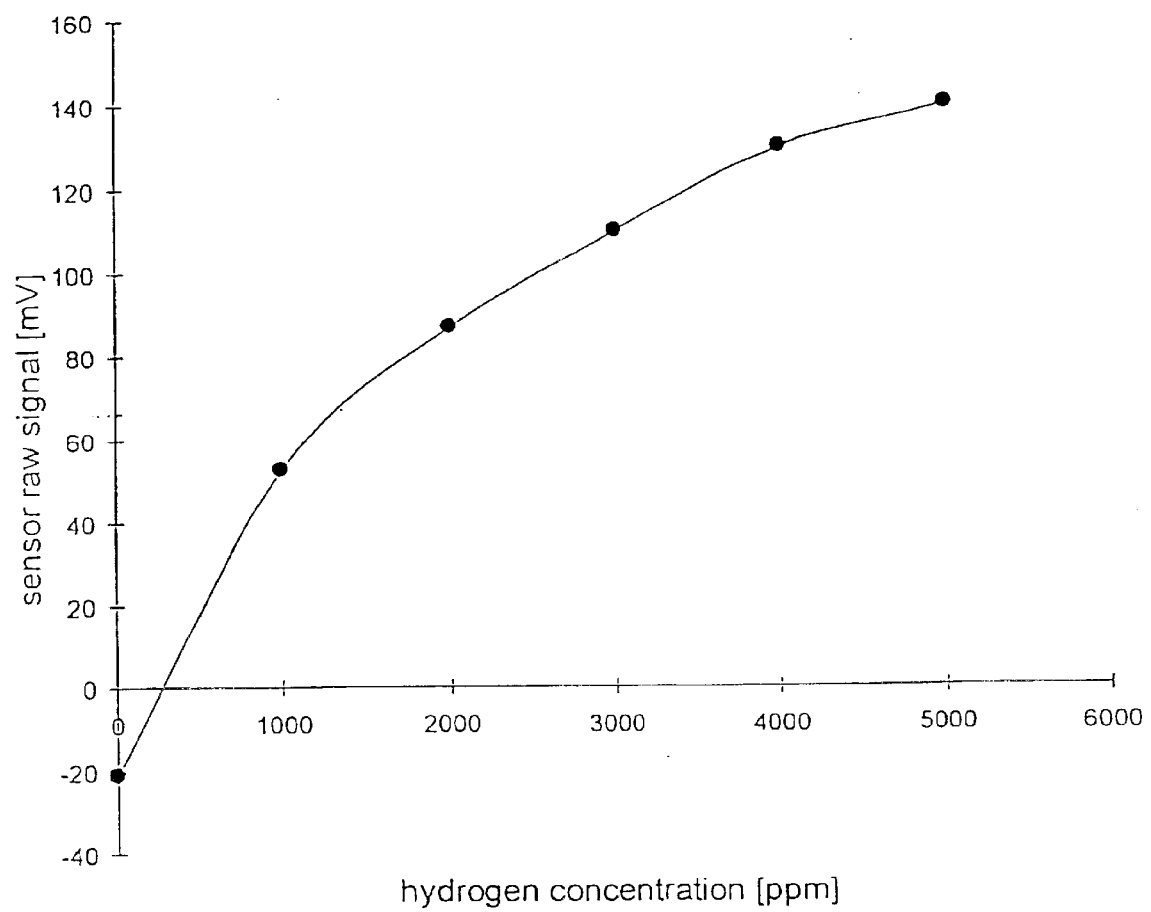
FIG. 8 is a graph which plots hydrogen concentration against the potential difference measured by an embodiment of an improved gas sensor.
Figure 9:
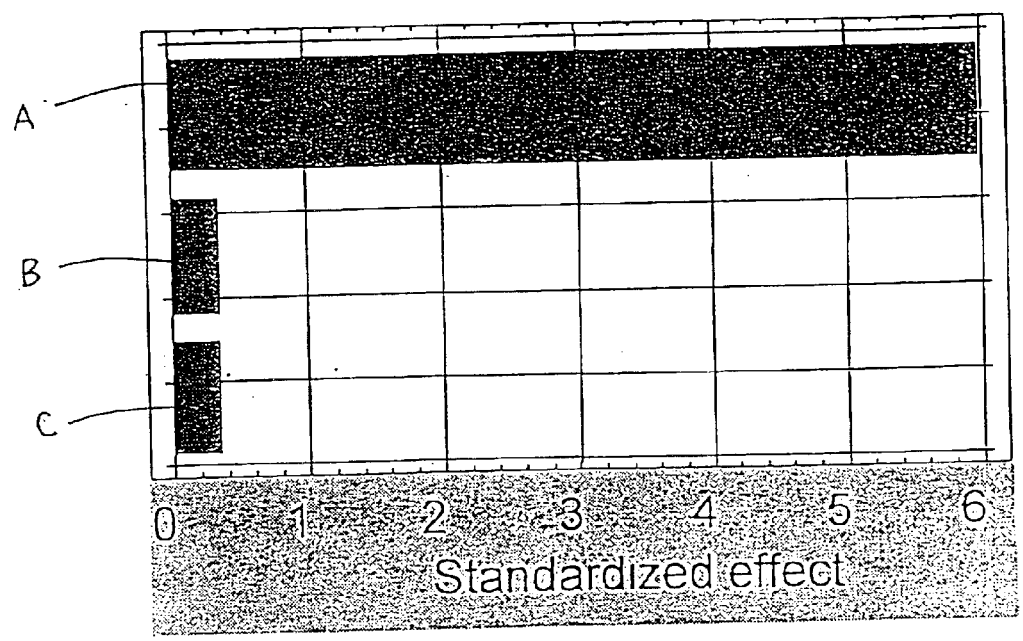
FIG. 9 is a standardized Pareto chart that shows the sensitivity of an improved gas sensor to changes in the composition of the atmosphere that the sensor is monitoring.

A preferred application of the present fuel cell assembly with an improved gas sensor is measuring hydrogen concentration in an oxidant stream exhausted from a fuel cell assembly. For this application, the preferred embodiment of the sensor comprises an active electrode, which in turn comprises platinum, and a passive electrode, which in turn comprises substantially pure gold. FIGS. 8 and 9 relate to data obtained from tests of a preferred embodiment of the sensor that is particularly suited for use as a hydrogen sensor for use with a solid polymer fuel cell.

FIG. 8 is a graph which plots hydrogen concentration against the potential difference measured by an embodiment of the sensor. The units of the vertical y-axis are millivolts and it represents the sensor raw signal, namely the potential difference measured between the active and passive electrodes. The units of the horizontal x-axis is parts per million (ppm) and it represents the hydrogen concentration. The following test conditions were used to obtain the data for this graph:

| | |
|---|---|
| Sensor type: | hydrogen sensor for fuel cell applications |
| Gas composition: | oxygen: 14.5 vol % <br> water: 31.0 vol % <br> hydrogen: 0–5000 ppm <br> nitrogen: remainder (that is, about 54.5 vol %) |
| Gas flow rate: | 100 liters/min. (about 26.4 gallons/min) |
| Temperature of sensor: | 400° C. (752° F.) |
| Temperature of gas: | 70° C. (158° F.) |
| Pressure: | 1.6 bar |

FIG. 8 shows a correlation between the sensor signal and hydrogen concentration, confirming that this embodiment of the sensor is well suited for measuring lean concentrations of hydrogen (that is, for example, less than 5000 ppm), in an atmosphere comprising mostly oxygen (more oxygen than necessary for complete hydrogen oxidation), water and nitrogen. Accordingly, an advantage of this preferred embodiment is that the sensor is particularly useful for measuring low hydrogen concentrations such as the concentrations that might be found in the oxidant stream exhausted from a fuel cell assembly.

FIG. 9 is a standardized Pareto chart, which shows the sensitivity of the sensor to changes in the composition of the atmosphere that the sensor is monitoring. Although a large portion of the gas is nitrogen, nitrogen does not participate in any of the reactions in the fuel cell or at the sensor electrodes, so changes in the amount of nitrogen do not influence the operation of the sensor. However, oxygen and water are reactants or products of the typical electrochemical reactions within a fuel cell and may thus be present at the sensor's active electrode. Accordingly, the amount of oxygen and water in the atmosphere can change depending upon the performance of the fuel cell. Therefore, it is important for the sensor to be insensitive to changes in the amount of oxygen and water in the atmosphere. The chart in FIG. 9 shows that changes in the amount of oxygen (bar B), between 2 and 21 vol %, or water (bar C), between low values close to zero and 50 vol %, have very little effect on the sensor in comparison to changes in the amount of hydrogen (bar A). This characteristic is another advantage of this preferred embodiment of the sensor.

While particular elements, embodiments and applications of the present invention have been shown and described, it will be understood, of course, that the invention is not limited thereto since modifications may be made by those skilled in the art without departing from the scope of the present disclosure, particularly in light of the foregoing teachings.

What is claimed is:

1. A fuel cell assembly comprising:
   (a) at least one fuel cell comprising:
      an anode;
      a cathode;
      an electrolyte interposed between said anode and said cathode;
      a fuel passage in fluid communication with said anode for directing a fuel stream to and from said anode;
      an oxidant passage in fluid communication with said cathode for directing an oxidant stream to and from said cathode; and
   (b) an electrochemical sensor associated with one of said fuel and oxidant passages for measuring the concentration of a gas in a respective one of said fuel and oxidant streams, said sensor comprising:
      an active electrode;
      a passive electrode;
      an electrolyte in contact with said active electrode and said passive electrode;
      a substrate upon which said electrolyte is disposed; and
      a heater in thermal contact with said substrate for heating said substrate and thereby heating said electrolyte.

2. The fuel cell assembly of claim 1 wherein said electrolyte is disposed on said substrate as a film with a thickness of less than 100 microns.

3. The fuel cell assembly of claim 2 wherein said electrolyte is disposed on said substrate as a film with a thickness of about 5 to 25 microns.

4. The fuel cell assembly of claim 1 wherein said passive electrode further comprises a coating that fluidly isolates said passive electrode from the surrounding atmosphere.

5. The fuel cell assembly of claim 4 wherein said coating comprises a material selected from the group consisting of a glass, a ceramic and a glass ceramic.

6. The fuel cell assembly of claim 1 wherein said electrolyte comprises a solid oxide electrolyte.

7. The fuel cell assembly of claim 1 wherein said electrolyte comprises a material selected from the group consisting of $ZrO_2$, $CeO_2$, $HfO_2$, yttrium-doped $ZrO_2$ and calcium-doped $ZrO_2$.

8. The fuel cell assembly of claim 7 wherein said substrate is unitary with said electrolyte, and both of said substrate and said electrolyte are made from the same material.

9. The fuel cell assembly of claim 1 wherein the average distance between said active and passive electrodes is between 0.1 millimeter and 10 millimeters.

10. The fuel cell assembly of claim 1 wherein said passive electrode and said active electrode each have a thickness between 0.0001 millimeter and 1 millimeter.

11. The fuel cell assembly of claim 10 wherein said active electrode comprises platinum and said passive electrode comprises gold.

12. The fuel cell assembly of claim 1 further comprising a device for measuring heater voltage and current for regulating said heater by calculating heater resistance by dividing said heater voltage by said heater current.

13. The fuel cell assembly of claim 1 further comprising a separate electrical circuit for measuring the temperature of said electrochemical sensor, and a temperature controller for changing the current or supply voltage of said heater.

14. The fuel cell assembly of claim 1 wherein said fuel cell is a solid polymer fuel cell.

15. The fuel cell assembly of claim 14 wherein said sensor is operatively associated with said oxidant passage, said gas is hydrogen and said sensor measures the concentration of hydrogen in said oxidant stream.

16. The fuel cell assembly of claim 1 wherein said sensor is located in said oxidant passage downstream of said cathode.

17. The fuel cell assembly of claim 1 further comprising an electrical circuit for measuring a voltage difference between said active electrode and said passive electrode.

18. The fuel cell assembly of claim 1 wherein said heater comprises a heating element comprising a resistor coil electrical circuit.

19. The fuel cell assembly of claim 1 wherein said heater comprises a coating that fluidly isolates said heater from the surrounding atmosphere.

20. The fuel cell assembly of claim 19 wherein said coating comprises glass, ceramic or glass ceramic.

21. The fuel cell assembly of claim 1 wherein said heater provides heat for raising the temperature of said electrolyte so that said electrolyte has an ion-conductance value greater than $10^{-4}(\Omega cm)^{-1}$.

22. The fuel cell assembly of claim 1 wherein said sensor is located within an interior oxidant or fuel stream passage within said fuel cell assembly.

23. The fuel cell assembly of claim 22 wherein said interior oxidant or fuel stream passage is located within an end plate of said fuel cell assembly.

24. The fuel cell assembly of claim 1 wherein said substrate comprises a thermally conductive electrical insulator.

25. The fuel cell assembly of claim 1 wherein said fuel cell assembly further comprises at least two electrochemical gas sensors, with a first electrochemical gas sensor for detecting a hydrogen gas concentration in said oxidant stream and a second electrochemical gas sensor for detecting an oxygen gas concentration in said fuel stream.

26. The fuel cell assembly of claim 1 further comprising a resistor associated with said heater for measuring temperature.

27. The fuel cell assembly of claim 1 wherein said sensor is operatively associated with said oxidant passage, whereby said heater is provided with heating energy from said at least one fuel cell.

* * * * *